United States Patent
Hawthorne et al.

(10) Patent No.: US 9,638,607 B1
(45) Date of Patent: May 2, 2017

(54) PORTABLE PHYSICAL PHASE STRATIFICATION AND SEPARATOR

(71) Applicant: H2A Environmental, Ltd., Keller, TX (US)

(72) Inventors: Michael Hawthorne, Keller, TX (US); Steve Fruendt, Keller, TX (US)

(*) Notice: Subject to any disclaimer, the term of this patent is extended or adjusted under 35 U.S.C. 154(b) by 433 days.

(21) Appl. No.: 14/522,034

(22) Filed: Oct. 23, 2014

Related U.S. Application Data

(60) Provisional application No. 61/947,807, filed on Mar. 4, 2014.

(51) Int. Cl.
*G01N 1/14* (2006.01)
*G01N 1/10* (2006.01)

(52) U.S. Cl.
CPC .............. *G01N 1/14* (2013.01); *G01N 1/10* (2013.01); *G01N 2001/1037* (2013.01)

(58) Field of Classification Search
None
See application file for complete search history.

(56) References Cited

U.S. PATENT DOCUMENTS

| | | | |
|---|---|---|---|
| 5,284,046 A * | 2/1994 | Jensen | B67D 7/085 73/1.31 |
| 6,138,462 A * | 10/2000 | Murray | B60H 1/00585 62/149 |
| 6,290,685 B1 | 9/2001 | Insley et al. | |
| 6,305,473 B1 | 10/2001 | Peramaki | |
| 6,468,335 B1 | 10/2002 | Polderman | |
| 7,364,661 B2 | 4/2008 | Puik | |
| 7,531,065 B2 | 5/2009 | Yamamoto | |
| 7,584,644 B2 * | 9/2009 | LaMontagne | G01F 25/0092 73/1.74 |
| 2013/0015052 A1 | 1/2013 | Vane et al. | |
| 2013/0325727 A1 * | 12/2013 | MacDonell | G06Q 10/30 705/308 |

* cited by examiner

*Primary Examiner* — Robert R Raevis
(74) *Attorney, Agent, or Firm* — Robert C. Montgomery; Montgomery Patent & Design, LP

(57) ABSTRACT

A portable physical phase stratification and separator device that includes a "U"-shaped frame connected to a fluid sump having a tank with an inlet port is disclosed. The inlet port is connected to a calibrated sampling column having a graduated cylinder by a gate valve. Above the sampling column is a vacuum port that selectively applies a vacuum to draw a fluid sample from a reservoir. The vacuum can be supplied by an external vacuum pump or by an internal venturi pump. The drawn fluid sample is directed into the cylinder where it separates. A sample of the drawn fluid can be extracted for external analysis. Various valves and fittings route pressures and vacuums and fluid sample as required around and out the portable physical phase stratification and separator device.

20 Claims, 11 Drawing Sheets

US 9,638,607 B1

PORTABLE PHYSICAL PHASE STRATIFICATION AND SEPARATOR

RELATED APPLICATIONS

This application claims the benefit of U.S. Provisional Application No. 61/947,807, which was filed Mar. 4, 2014, the entire disclosures of which are incorporated herein by reference.

FIELD OF THE INVENTION

The presently disclosed subject matter relates to physical phase stratification and separator device. More particularly, it relates to portable phase stratification and separator devices that draw samples from subterranean reservoirs to enable analysis of the sample's constituent components.

BACKGROUND OF THE INVENTION

Many industrial operations present potentials for environmental hazards because they can produce unacceptable levels of contamination during their operation. To mitigate such hazards State and Federal laws often require active monitoring and remediation of environmental contamination. Sometimes such monitoring and remediation requires drawing fluid samples from subterranean reservoirs to enable analysis and examination of the non-aqueous phase liquids (NAPLs) in the reservoir.

NAPL's typically do not mix well with water. Such mixing incompatibilities result is sets of material properties that can be exploited via phase stratification and separation for sampling, monitoring, and analyses of the NAPLs. In the prior art phase stratification and separation was typically performed using on-site sampling devices and off-site analysis of the samples. This use of on-site and then off-site devices and agencies was rather expensive and slow, could lead to erroneous results, and separated the gathering and analysis in a manner that was often not conducive to the needs of site personal and government monitors.

In view of the foregoing problems with prior art phase stratification and separation it would be advantageous to have a portable device that could sample on-site and on-demand and that could enable fast analytical results. Beneficially such a portable phase stratification and separation device could perform NAPL sampling and analysis quickly and easily. Ideally such a portable phase stratification and separation device would be both cost effective and accurate.

SUMMARY OF THE INVENTION

The principles of the present invention provide for portable phase stratification and separation devices that can perform on site sampling and analysis of NAPL samples quickly, easily, and in a cost effective manner.

A portable sampling device that is in accord with the present invention includes a "U"-shaped frame having a first vertical element, a second vertical element and a brace across the tops of the first vertical element and the second vertical element. The vertical element has a first free end while the second vertical element has a second free end. The device further includes a fluid sump having a tank that is connected to the first free end and to the second free end. The tank includes a top inlet valve fitting for allowing fluid into the tank and wheels that are operatively attached to the tank. A calibrated sampling column having a graduated cylinder is attached to the frame above the fluid sump. A cylinder base is operatively connected to the inlet valve fitting while a gate valve is disposed between the cylinder base and the sampling column. The gate valve is for selectively allowing fluid to drain from the graduated cylinder into the tank.

In practice a "U"-shaped support arm can be attached to the first vertical element and to the second vertical element to act as a handle. The wheels may be attached to the tank by an axle mount and an axle and the tank may have a sight tube. In addition, the tank may be fitted with a purge fitting for passing material into the tank; a pipe cross operatively connected to the purge fitting, and an air inlet valve that is attached to the pipe cross. The air inlet valve can then selectively enable air to pass through the pipe cross into the tank. A purge gauge can then be connected to the pipe cross for displaying pressure in the tank. In that case an equalization valve that operatively connects the pipe cross to an equalization tube can be used for selectively equalizing pressure in the tank with pressure in the equalization tube.

The portable sampling device may also include a drain fitting that is operatively connected to the bottom of the tank, a drain hose assembly operatively connected to the drain fitting, and a three-way drain diverter valve that is operatively connected to the drain fitting. The drain diverter valve for selectively allows fluid in the tank to drain. A sampling valve that is operatively connected to the cylinder base can be included. The purpose of the sampling valve is to selectively passing fluid in the graduated cylinder into an external container.

The portable sampling may further include a vacuum cross that is operatively connected to the top of the graduated cylinder, and a cylinder gauge that is attached to the vacuum cross for measuring the pressure in the vacuum cross. The vacuum cross may also include a vacuum port for receiving a vacuum and an inlet port for receiving drawn fluid.

The vacuum port may be operatively connected to a vacuum shut off valve in which the vacuum shut off valve selectively applies a vacuum to the vacuum port from an external vacuum pump. The vacuum port may also be operatively connected to a pump valve via an expansion chamber such that the pump valve selectively applies a vacuum to the vacuum port from a venturi pump. The vacuum cross may also include a vent port that is operatively connected to a vent valve for selectively venting pressure in the vacuum cross.

The inlet port may selectively receive an input chemical that is selectively passed by a chemical injection valve. That input chemical might be a demulsifier. The inlet port may receive a fluid drawn by vacuum from a reservoir.

BRIEF DESCRIPTION OF THE DRAWINGS

The advantages and features of the present invention will become better understood with reference to the following more detailed description and claims taken in conjunction with the accompanying drawings in which like elements are identified with like symbols and in which:

Figure 1:
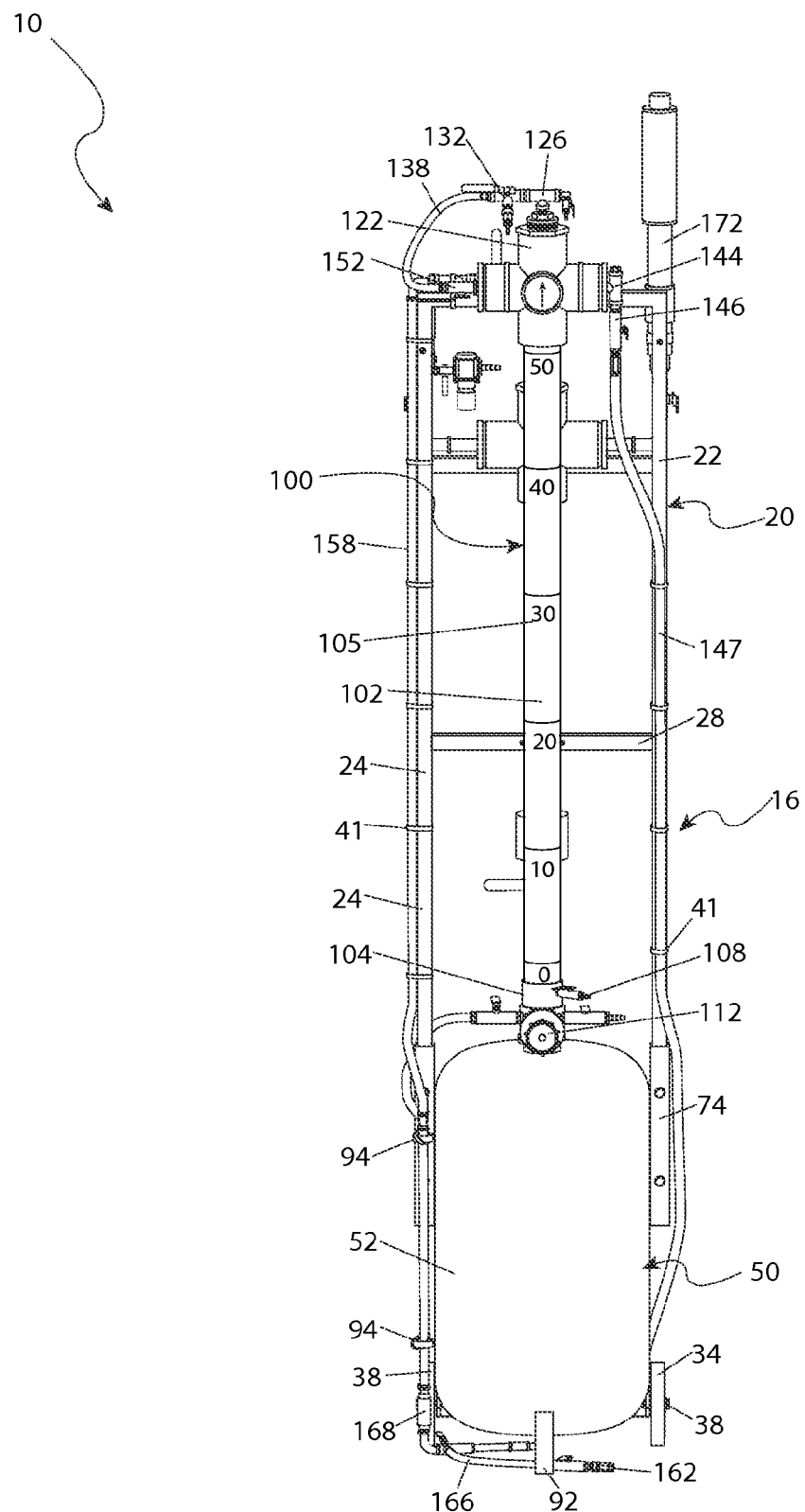
FIG. 1 is an isometric view of a portable analysis device 10 that is in accord with a preferred embodiment of the present invention.

DESCRIPTIVE KEY 10 portable analysis device
16 transport cart
20 handle frame
22 first vertical element
24 second vertical element
26 first brace
28 second brace
30 support arm
32 handle fastener
34 wheel
36 axle
38 retainer
41 tie
42 "U"-bolt
50 fluid sump
52 tank
54 inlet valve fitting
56 purge fitting
58 pipe cross
61 drain
62 supply port
64 air inlet valve
66 purge gauge
68 equalization valve
72 drain fitting
74 sleeve
82 lower sight tube fitting
84 upper sight tube fitting
86 sight tube
88 drain diverter valve
92 stand
94 holder
96 axle mount
100 sampling column
102 graduated cylinder
104 cylinder base
105 indicia
106 sampling port
108 sampling valve
109 sampling fitting
112 gate valve
114 first end
116 second end
122 vacuum cross
124 inlet port
126 upper tee
127 pipe
128 chemical injection valve
129 chemical injection port
132 well diverter valve
134 well inlet coupling
138 by-pass hose
142 vacuum port
144 vent port
146 vent valve
147 vent hose
148 cylinder gauge
152 suction diverter valve
154 equalization tube
156 suction tee
158 multi-purpose hose
162 site vacuum coupler
164 site vacuum shut off valve
166 vacuum transfer hose
168 check valve
172 first vacuum pump
174 first air inlet
176 first pump valve
178 first pump clamp
182 clamp fastener
184 clamp securing fastener
186 first pump elbow
192 second vacuum pump
194 second air inlet
196 air inlet regulator
198 air supply valve
202 second pump clamp
204 second pump valve
206 second pump elbow
210 fluid knock out assembly
212 expansion chamber
214 first pump inlet
216 second pump inlet
218 expansion gauge
222 knock out tube
223 knock out base
224 disposal valve
226 disposal fitting
228 top port
232 vacuum routing hose
234 secondary vacuum shut-off valve
238 hose clamp
400 holding tank
405 site vacuum pump
410 drain hose assembly

DETAILED DESCRIPTION OF THE PREFERRED EMBODIMENT

Figure 9:
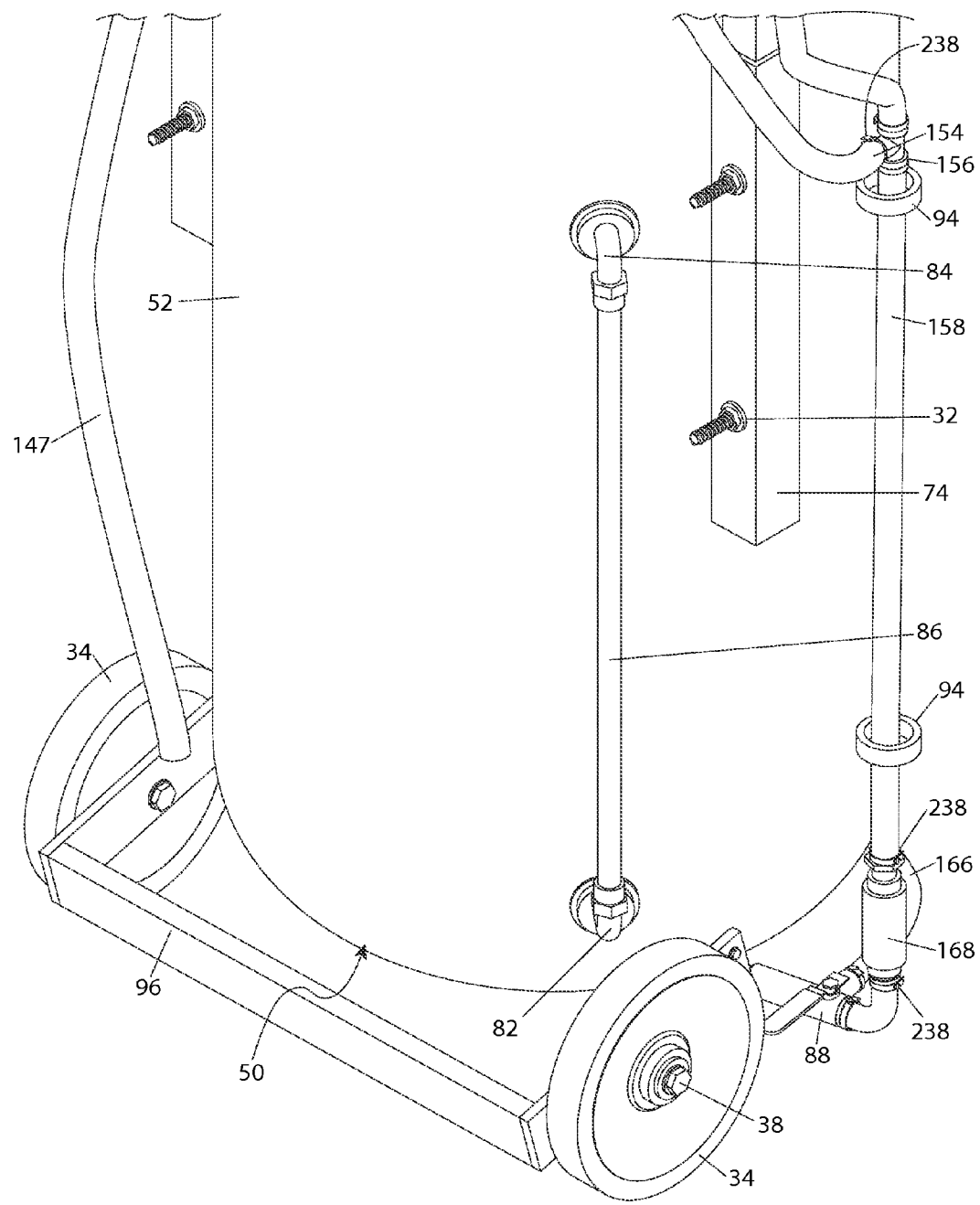
FIG. 9 is a detail view of the fluid sump 50, particularly showing a sight tube 86 used in the portable analysis device 10 shown in FIGS. 1 and 2.
Figure 10:
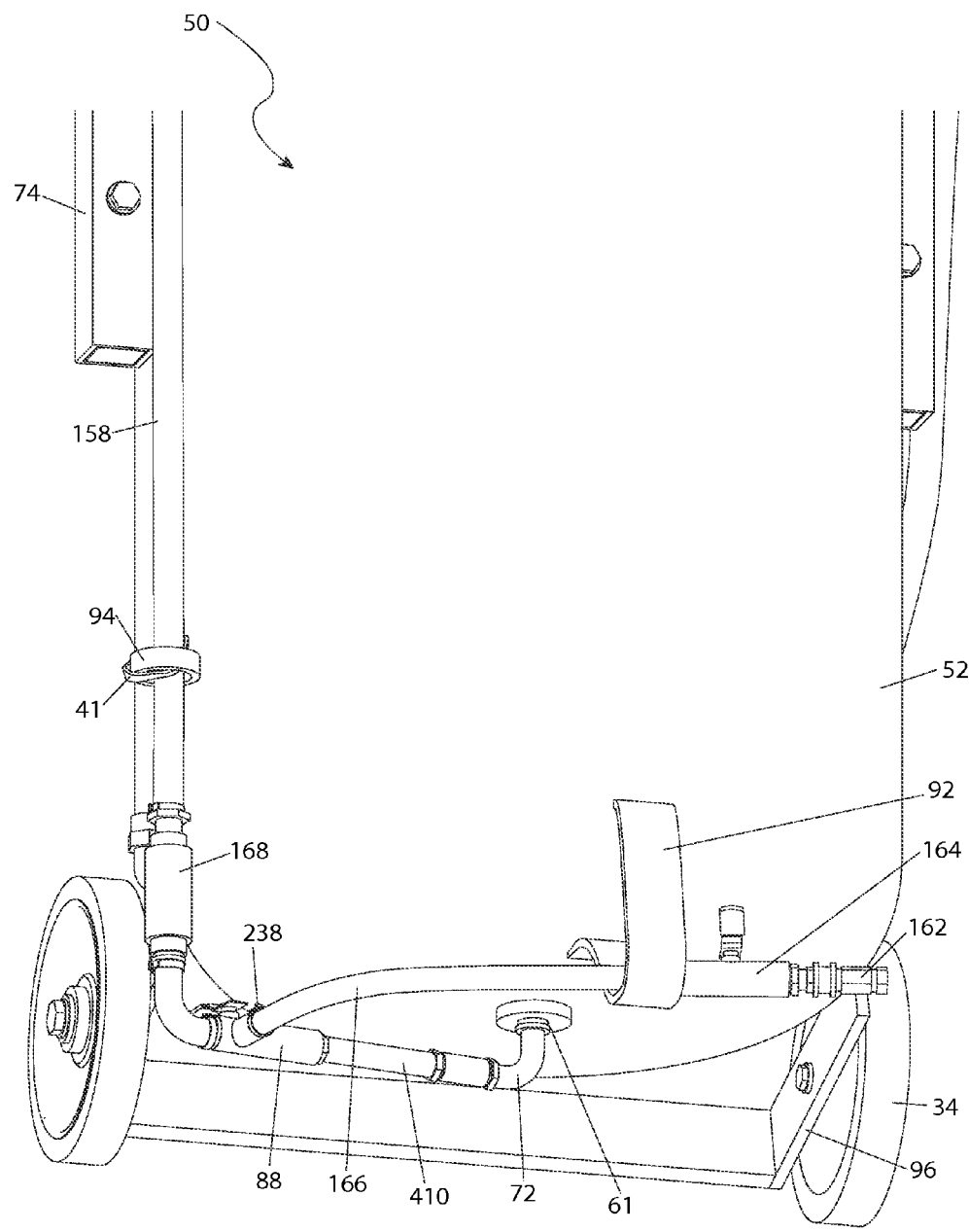
FIG. 10 is a detail view of the bottom of the fluid sump 50 and a drain valve 88 used in the portable analysis device 10 shown in FIGS. 1 and 2; and, FIG. 11 is a block diagram of the process flow of the portable analysis device 10 when used in accordance with a preferred embodiment of the present invention.
Figure 11:
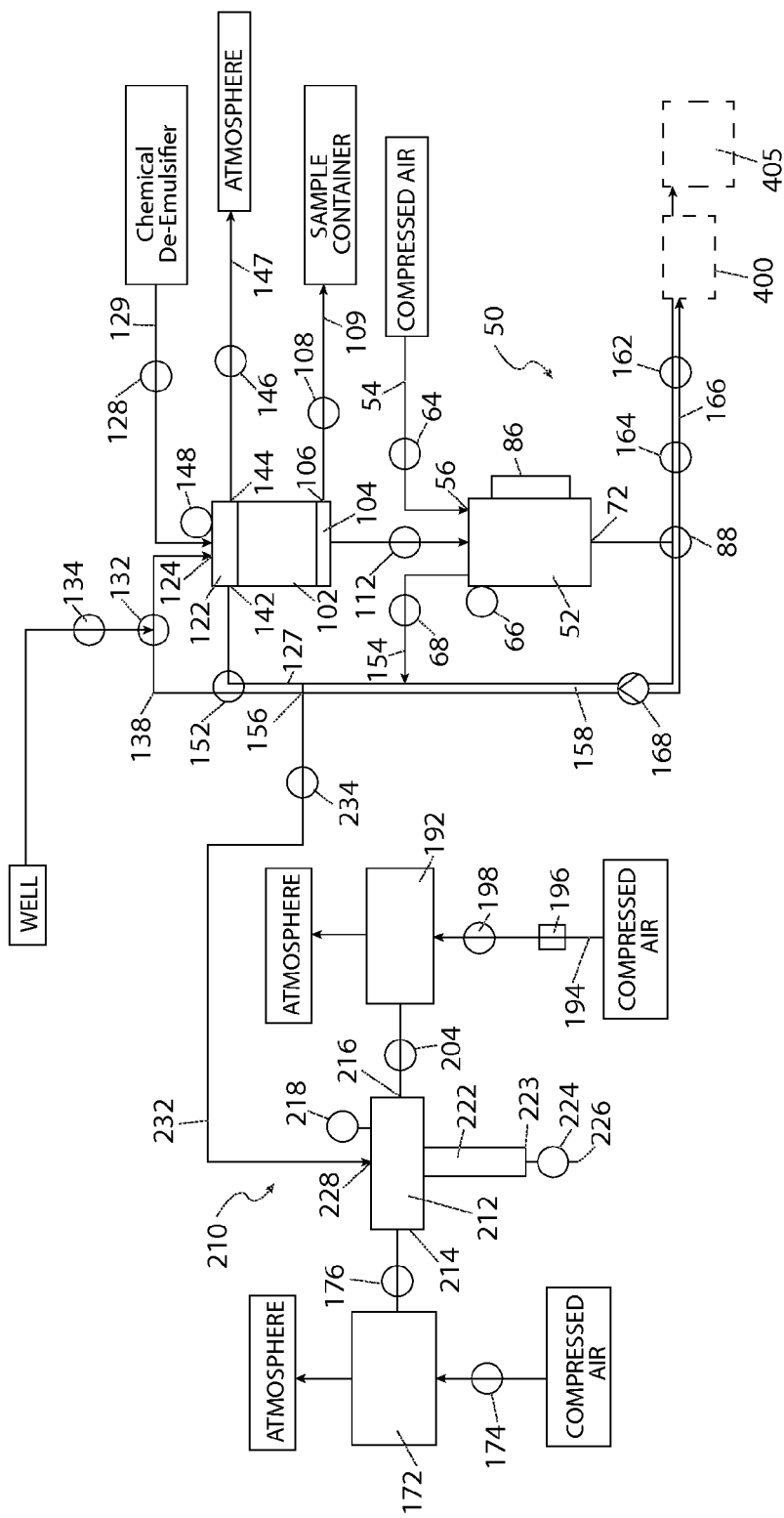

The preferred embodiment of the present invention is physically depicted in FIGS. 1 through 10 and its operation is illustrated in FIG. 11. However, the invention is not limited to what is specifically illustrated and described. A person skilled in the art will appreciate that many other embodiments of the invention are possible without deviating from the basic concept of the invention. Any such work around also falls with the scope of this invention.

The terms "a" and "an" herein do not denote a limitation of quantity, but rather denote the presence of at least one (1) of the referenced items. In addition, unless otherwise denoted all directional signals such as up, down, left, right, inside, outside are taken relative to the illustration shown in FIG. 1.

The present invention describes a portable physical phase stratification and separator device (hereinafter referred to as a "portable analysis device 10") which can be easily transported to a test site, can be used to draw a sample of fluid from a subterranean reservoir, allows that fluid to separate by density into constituent components in a calibrated sampling column, and can be used to measure those components as a volume of the total sample. In addition, samples or separated portions of a sample can be removed from the portable analysis device 10 and placed into a container for further laboratory analysis.

Figure 2:
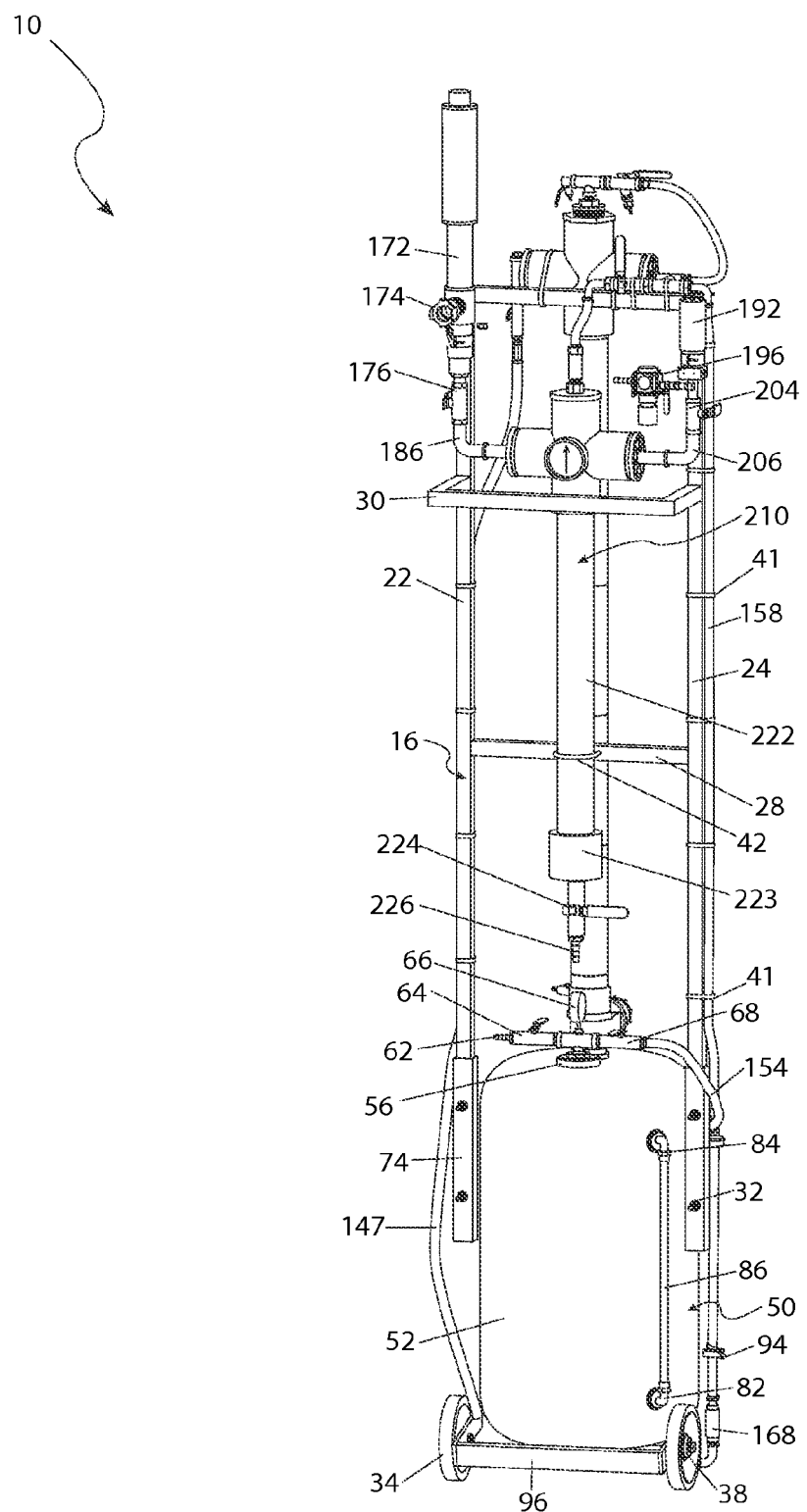
FIG. 2 is an isometric view of the rear of the portable analysis device 10 shown in FIG. 1.

FIG. 1 presents an isometric view of the front of a portable analysis device 10 that is in accord with the present invention, while FIG. 2 presents an isometric view of its rear. The portable analysis device 10 includes a calibrated sampling column 100 that is mounted to a fluid sump 50. The fluid sump 50 and the column 100 and the other subsequently described elements attach to a transport cart 16.

Figure 3:
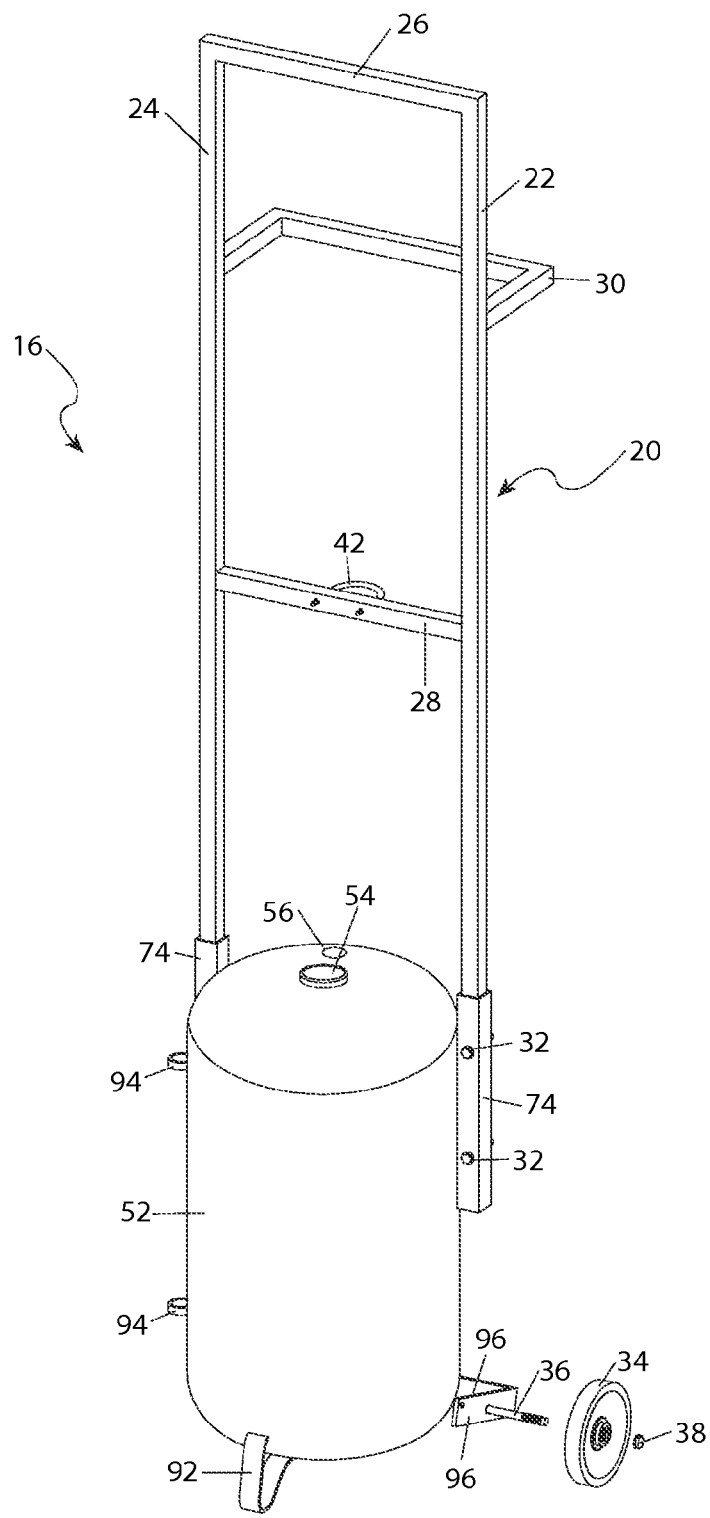
FIG. 3 is an isolated view of a transport cart 16 used in the portable analysis device 10 shown in FIGS. 1 and 2.

Referring now primarily to FIG. 3, the transport cart 16 includes a handle frame 20 having a first vertical element 22 and a second vertical element 24 that are attached at their upper ends to a first brace 26, thereby forming an inverted "U" arrangement. The first vertical element 22, the second vertical element 24, and the first brace 26 are preferably square metal tubing having a protective coating or plating to inhibit corrosion. However, it should be understood that other materials, including some thermoplastics, or other shapes, may be utilized. The first vertical element 22, the second vertical element 24, and the first brace 26 are preferably mitered at their conjoined ends and then welded together to present a smooth fabrication. At their other ends the first vertical element 22 and the second vertical element 24 each include a handle aperture (which are not specifically shown) that receives handle fasteners 32 that secure the handle frame 20 to sleeves 74 on the sides of a steel tank 52.

Still referring primarily to FIG. 3, a second brace 28 is connected (preferably by welding) to the midpoints of the first vertical element 22 and the second vertical element 24. The second brace 28 is preferably made of the same material as the first vertical element 22, the second vertical element 24, and the first brace 26. The second brace 28 includes two apertures that receive a "U"-bolt 42 with fasteners. As explained in more detail subsequently the "U"-bolt 42 supports a fluid knock out assembly 210. Between the first brace 26 and the second brace 28 is a "U"-shaped support arm 30 that is attached to the rear faces of the first vertical element 22 and the second vertical element 24.

Turning now to FIGS. 1-3 as required, the fluid sump 50 includes the tank 52, which is equipped with various fittings and ports as necessary to accomplish its intended task. The tank 52 is generally cylindrical but has a slightly domed shaped top and bottom. In practice the tank 52 holds approximately eight gallons (8 gal) and is pressure rated to at least fifteen pounds per square inch (15 psi). Disposed on the lower end of the tank 52 is an axle mount 96 for an axle 36 (also see FIGS. 9 and 10). The axle 36 receives wheels 34 which are secured to the axle 36 by retainers 38 which may be threaded nuts, snap rings, or similar fasteners. The wheels 34 are preferably solid, ribbed, rubber tires captured in pressed steel rims that mount to the axle 36 using sealed ball bearings (not shown).

On the bottom of the tank 52 opposite the axle mount 96 is a stand 92. The stand 92 is preferably a formed steel piece welded to the tank 52 to form a three-point support in conjunction with the wheels 34. The portable analysis device 10 uses the three-point support when in use or when in storage to keep the tank 52 vertical.

Located along the upper periphery of the tank 52 are the sleeves 74 that accept the lower end of the first and second vertical elements 22 and 24. The sleeves 74 have sleeve apertures (not shown as they are covered by the handle fasteners 32) that are spaced apart to enable alignment with the apertures through the first vertical element 22 and the second vertical element 24. With the support arm 30 oriented away from the tank 52 the first vertical element 22 and the second vertical element 24 are inserted into respective sleeves 74 until the handle apertures (not shown) align with the sleeve apertures (also not shown). Handle fasteners 32 are then inserted through the aligned apertures to secure the handle frame 20 to the tank 50. The support arm 30 is used as a grasping point to manipulate the portable analysis device 10.

Referring now primarily to FIGS. 2 and 9, the periphery of the tank 50 has an upper sight tube fitting 84 and a lower sight tube fitting 82. The upper sight tube fitting 84 and the lower sight tube fitting 82 are inserted into the tank 52 via threaded ports that conform to National Pipe Thread standards. The upper and lower sight tube fittings 82, 84 include elbows having straight pipe threads on a first end and compression fittings on the other. The upper and lower sight tube fittings 82, 84 are aligned and then a sight tube 86 is connected between to the compression fittings. The sight tube 86 is preferably transparent plastic tubing and is used to provide a visual indication of the level of fluid in the tank 52. Glass may also be used.

Figure 8:
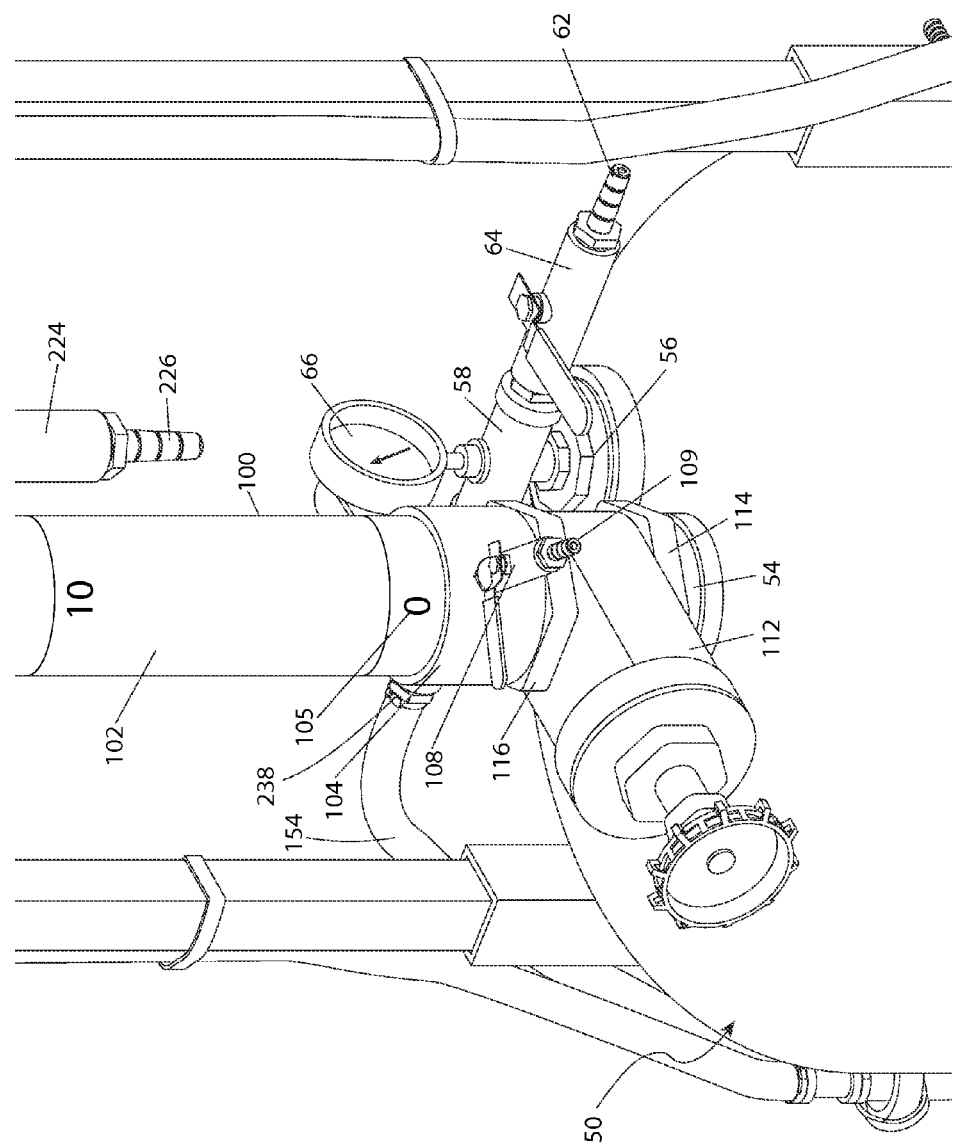
FIG. 8 is a detail view of the top of a fluid sump 50, the bottom of the graduated cylinder 102, and a gate valve 112 used in the portable analysis device 10 shown in FIGS. 1 and 2.

Turning now to FIGS. 3 and 8, centrally located at the top of the tank 52 is a threaded inlet valve fitting 54. The inlet valve fitting 54 receives the first end 114 of a gate valve 112.

Disposed at the top of the tank 52 in proximity to the inlet valve fitting 54 is a purge fitting 56. Attached to the purge fitting 56 by pipe threads is a pipe cross 58. This pipe cross 58 has four (4) female ports. The first attaches the pipe cross 58 to the purge fitting 56. A second port receives an air inlet valve 64. The air inlet valve 64 is a standard ball valve having a handle that either allows compressed air from an external source (15 PSI max, see FIG. 11) to pass through the air inlet valve 64 or to block the flow. At the input to the air inlet valve 64 is a quick-connect supply port 62 fitting used to connect to the external source. A purge gauge 66 is attached to the third port of the pipe cross 58. The purge gauge 66 is capable of measuring both positive pressure and a vacuum within the pipe cross 58 and in the tank 52.

Figure 7:
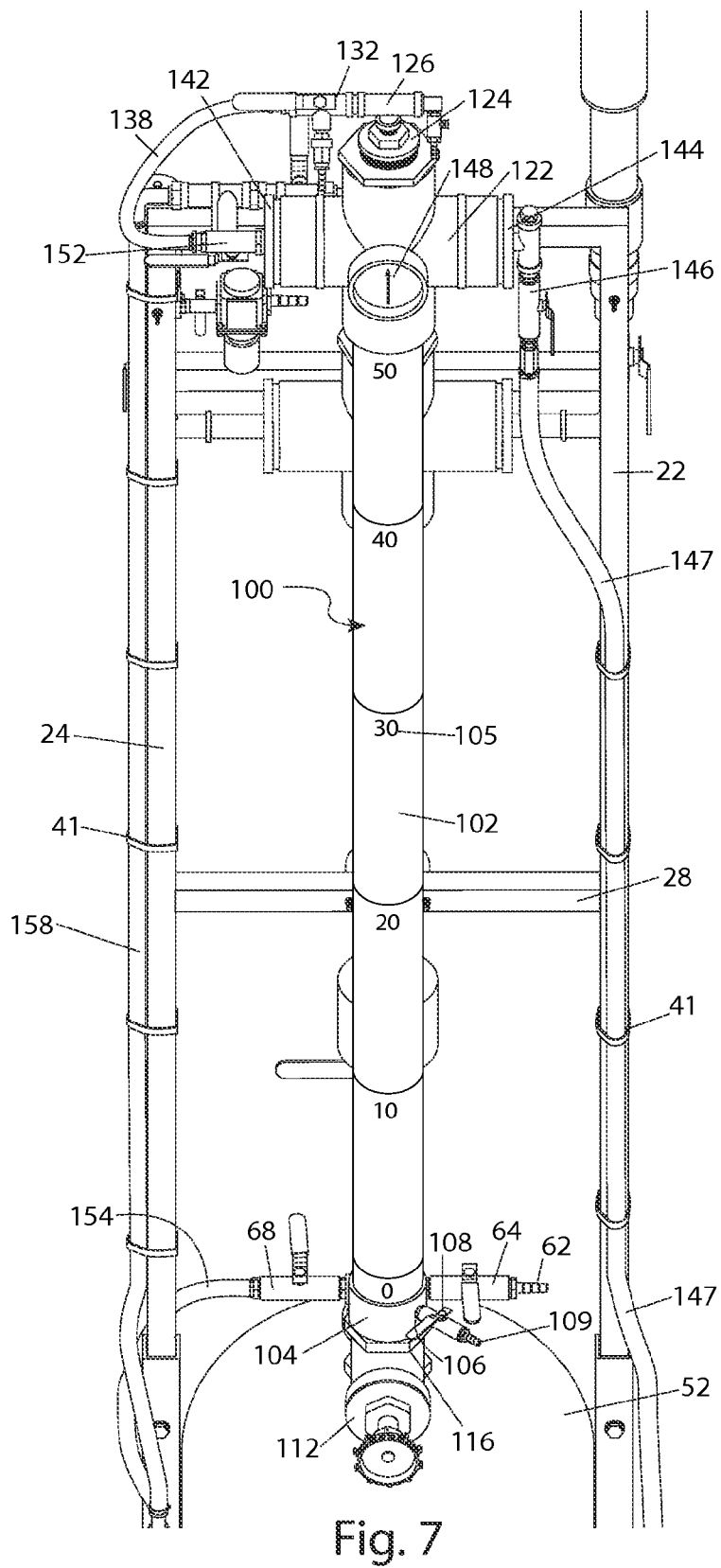
FIG. 7 is a detail view of a graduated cylinder 102 used in the portable analysis device 10 shown in FIGS. 1 and 2.

Referring now to FIG. 7 the fourth port of the pipe cross 58 connects to an equalization valve 68. The equalization valve 68 is a standard ball valve which can be manipulated by a handle to either allow equalization of pressure or vacuum in the tank 52 with the conditions in an equalization tube 154 or to seal the tank 52. The equalization tube 154 is connected to a pipe nipple threaded into the equalization valve 68 by means of a hose clamp 238 at a first end and to a suction tee 156 (see FIG. 9) in the multi-purpose hose 158 by means of another hose clamp 238 at a second end. The equalization tube 154 and the multi-purpose hose 158 may conveniently be routed through any of the holders 94 disposed on the side of the tank 52 and secured with plastic ties 41.

Turning now to FIG. 10, disposed at the center of the bottom dome of the tank 52 is a drain 61. The drain 61 is connected by a drain fitting 72 and a drain hose assembly 410 to a first cross port of a drain diverter valve 88. The drain diverter valve 88 is a three-way diverter valve that functions as a pipe tee with the added feature of selectively routing fluid from its post port to either, but not both cross ports. The drain diverter valve 88 has a handle that can be used to either allow fluid from the drain fitting 72 to pass to a vacuum transfer hose 166 or to allow fluid from the multi-purpose hose 158 to pass to the vacuum transfer hose 166.

Referring now to FIGS. 1-5 and 9-10, on the sides of the tank 52 below the sleeves 74 are a plurality of holders 94. The holders 94 are rings that are best attached to the tank 52 by welding. The holders 94 are configured to retain hoses or hose/fitting combinations by using plastic ties 41.

FIG. 8 shows the sampling column 100 on top of the gate valve 112. The sampling column 100 is connected to the second end 116 of the gate valve 112 by male threads (not shown) that are located at the lower end of a cylinder base 104. The cylinder base 104 is preferably a cylindrical, thermoplastic adaptive fitting configured with an unthreaded female port at its upper end and the male threads at its lower end.

Turning now to both FIGS. 7 and 8, a graduated cylinder 102, preferably a polycarbonate cylinder is affixed to the unthreaded female port of the cylinder base 104. Other materials, such as acrylics, or carbon nanotubes, and other methods of attachment may also be used. It is envisioned that indicia 105 such as, but not limited to, lines and numerals arranged in a uniform pattern will be disposed on the graduated cylinder 102. Such indicia provide an indication of the volume of fluid or stratified fluid in the sampling column 100.

Disposed in the periphery of the cylinder base 104, preferably oriented perpendicularly to the stem of a gate valve 112 is a female sampling port 106 threaded to National Pipe Thread standards. A sampling valve 108 is attached at a first end to the sampling port 106 by an appropriate pipe fitting. A sampling fitting 109 is attached to a second end of the sampling valve 108. The sampling valve 108 is preferably a standard ball valve which can be manipulated by a handle to either allow fluid contained within the graduated cylinder 102 to pass through the sampling fitting 109 or to block fluid from the sampling port 106 to prevent flow. The sampling fitting 109 is an open fitting which allows fluid contained in the graduated cylinder 102 to be collected into a container for further analysis.

Figure 6:
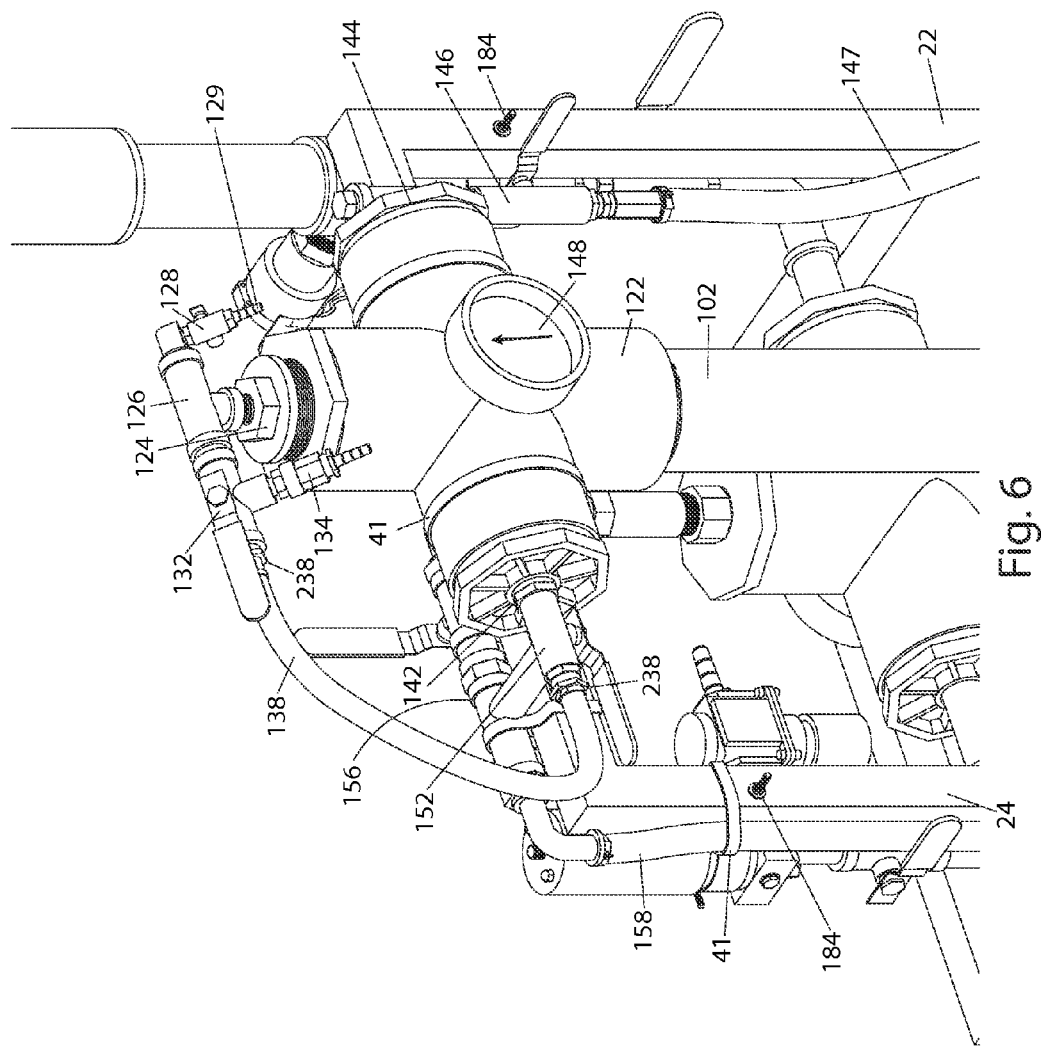
FIG. 6 is a detail view of the upper end of the sampling column 100 used in the portable analysis device 10 shown in FIGS. 1 and 2.

Referring now to FIGS. 6 and 7, at the upper end of the graduated cylinder 102 is a vacuum cross 122. The vacuum cross 122 is beneficially a thermoplastic pipe fitting configured to have four (4) uniformly sized unthreaded female ports and one (1) aperture. Disposed in one side wall of the vacuum cross 122 is a one quarter inch National Pipe Thread (¼ in. NPT) threaded female aperture (not shown) into which a cylinder gauge 148 is connected. The cylinder gauge 148 preferably can measure the vacuum or the positive pressure in the vacuum cross 122. A first port of the vacuum cross 122 is affixed to the upper end of the graduated cylinder 102. A second port of the vacuum cross 122 is configured as a vacuum port 142. The vacuum port 142 is reduced to the appropriate diameter for a vacuum source to draw fluid from the vacuum cross 122. The drawn fluid enters the vacuum cross 122 through a third port which is the inlet port 124.

The inlet port 124 is located directly opposite the graduated cylinder 102 such that any fluid entering the vacuum cross 122 will experience a change in pressure due to the increased cross-sectional area of the vacuum cross 122 in comparison to the fittings in the inlet port 124, and thus drop into the graduated cylinder 102. An upper tee 126 is connected to the inlet port 124 by reducer fittings and a pipe nipple. The upper tee 126 is a standard one half inch (½ in.) pipe tee that is configured to be attached at the post port to the pipe nipple. The fourth port of the vacuum cross 122 is a vent port 144. The vent port 144 is reduced to connect to a vent valve 146. The vent valve 146 is preferably a standard one quarter inch (¼ in.) ball valve which can be manipulated by a handle to either allow air to pass through the internal chamber to or from the atmosphere or to block the chamber. A vent hose 147 is connected to the vent valve 146 to direct liquid in the vent stream away from a user.

The vent hose 147 may be conveniently secured to the first vertical element 22 with at least one (1) tie 41. In addition, the vacuum cross 122 is secured to the first brace 26 of the transport cart 16 with ties 41. The ties 41 are configured to encircle the vacuum port 142 and the first brace 26 (as well as the vent port 144 and the first brace 26) as illustrated in FIG. 6.

Still referring to FIGS. 6 and 7, a chemical injection valve 128 is connected to the first cross port of the upper tee 126. A chemical injection port 129 is connected to the chemical injection valve 128. The chemical injection port 129 is preferably a quick-disconnect fitting through which a liquid demulsifier can be introduced by vacuum or positive pressure into the graduated cylinder 102. The chemical injection valve 128 is preferably a standard ball valve which can be manipulated by a handle to either allow or block the flow of the demulsifier.

A well diverter valve 132 is connected to the second cross port of the upper tee 126. A well inlet coupling 134 is connected to a post port of the well diverter valve 132. The well inlet coupling 134 is a quick-disconnect fitting through which liquids from a subterranean reservoir can enter the portable analysis device 10. The well diverter valve 132 is a standard three-way diverter valve which can be manipulated by a handle to either allow fluid from the well inlet coupling 134 to pass through its internal passageway to the upper tee 126 or to allow fluid from the well inlet coupling 134 to pass through an internal passageway to a first end of a by-pass hose 138.

The by-pass hose 138 is preferably a plastic hose connected at a first end to a pipe nipple that is threaded into the second cross port of the well diverter valve 132 and secured by a hose clamp 238. The second end of the by-pass hose 138 is connected to a pipe nipple that is threaded into a first cross port of a suction diverter valve 152 and then secured with a hose clamp 238. In turn, the suction diverter valve 152 is connected to the vacuum port 142 of the vacuum cross 122 by pipe fittings.

Figure 4:
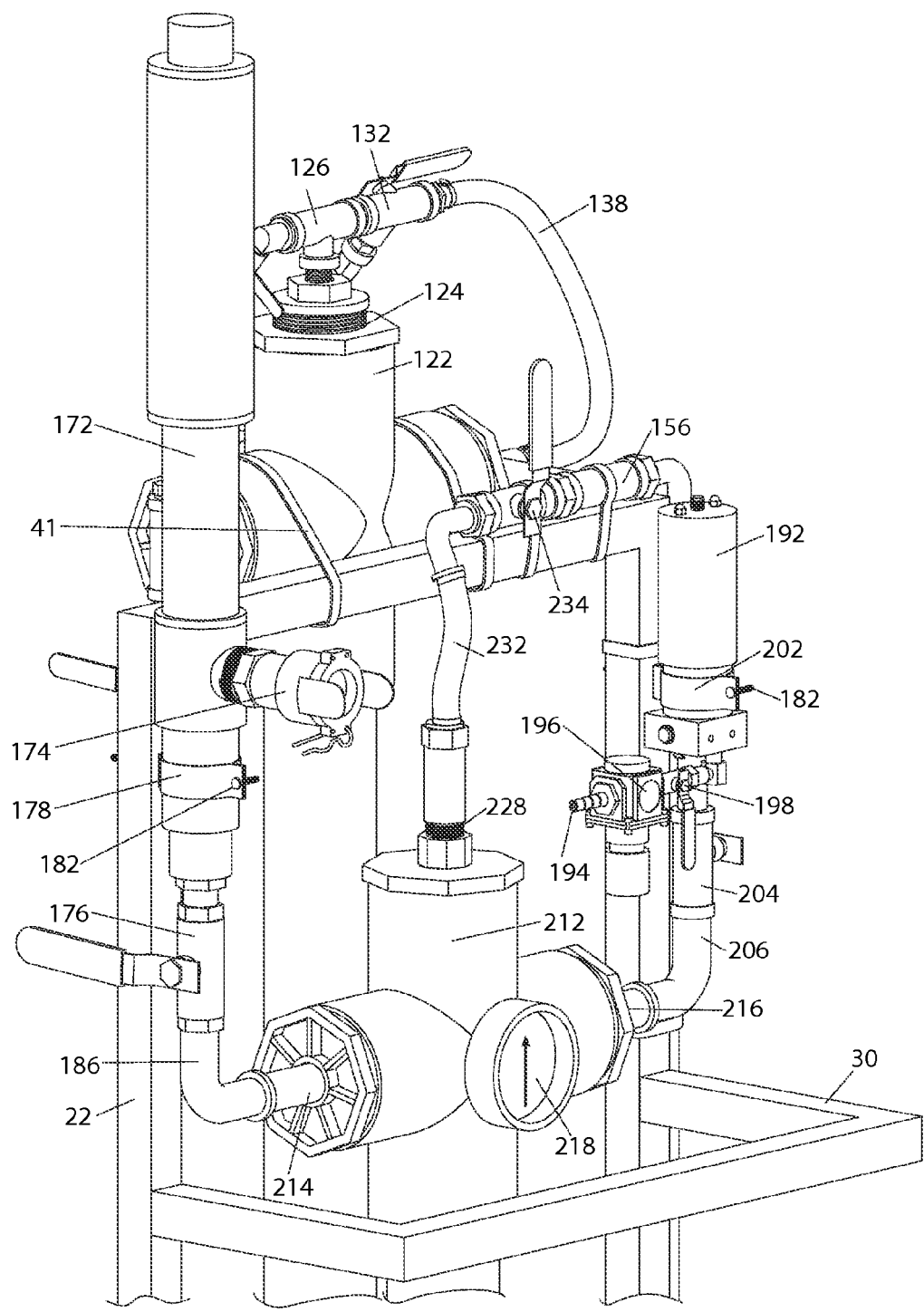
FIG. 4 is a detail view of a first vacuum pump 172, a well inlet coupling 134, and a sampling column 100 used in the portable analysis device 10 shown in FIGS. 1 and 2.
Figure 5:
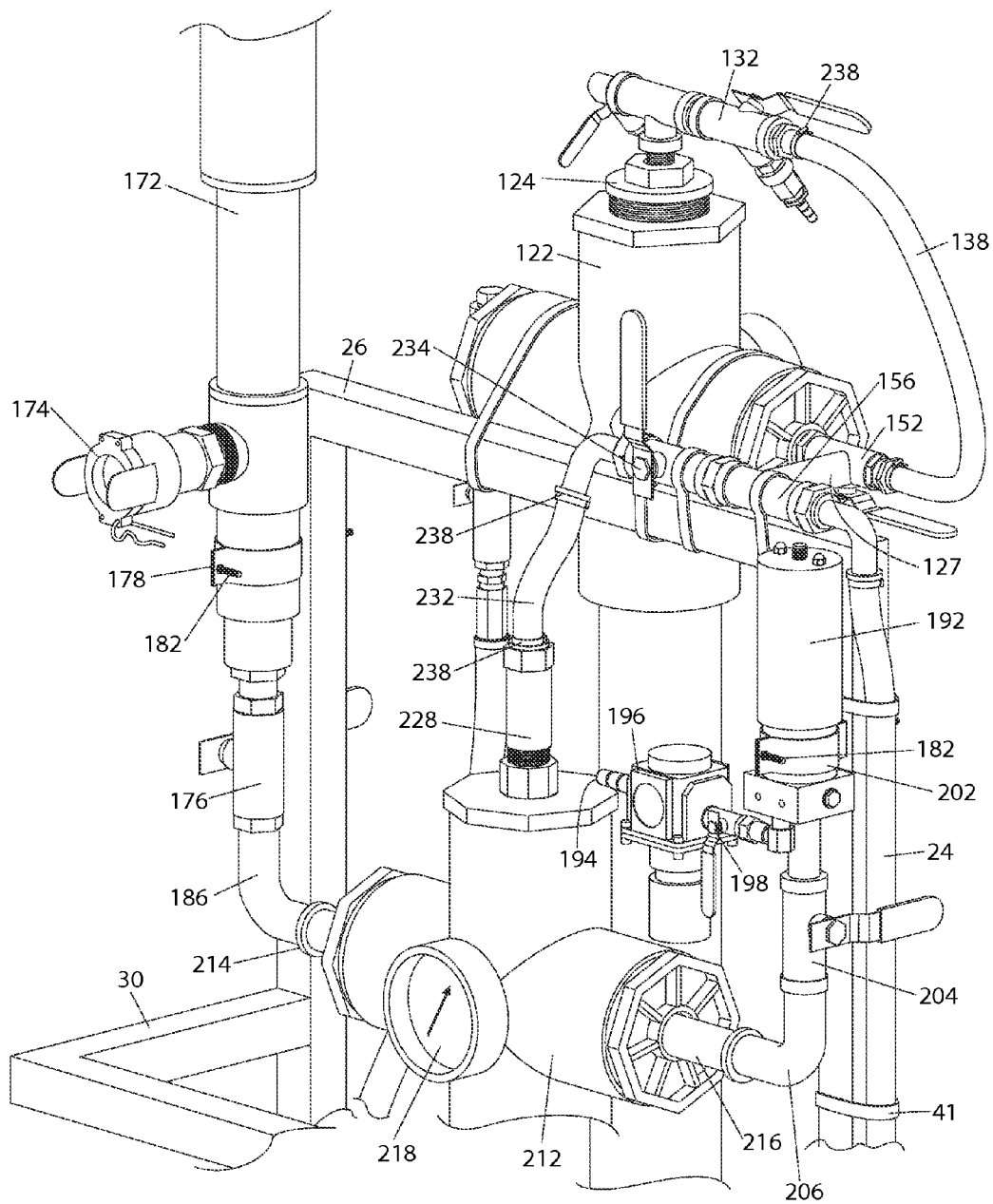
FIG. 5 is a detail view of a second vacuum pump 192, an air inlet regulator 196, and a fluid knock out assembly 210 used in the portable analysis device 10 shown in FIGS. 1 and 2.

Turning now to FIGS. 4 and 5, a post port of the suction tee 156 is connected to a post port of the suction diverter valve 152 with an appropriately sized pipe 127. The suction diverter valve 152 is preferably a standard three-way diverter valve which can be manipulated by a handle to either allow a vacuum from the suction tee 156 to be applied through an internal passageway to a second end of the by-pass hose 138 or to allow a vacuum from the suction tee 156 to be applied through an internal passageway to the vacuum port 142 of the vacuum cross 122.

The motive power to draw fluid from a subterranean reservoir into the portable analysis device 10 can be applied by three (3) different sources. The first is an on-site vacuum pump 405 that is installed above ground at the work site, reference FIG. 11. The on-site vacuum pump 405 might be configured to draw a vacuum across a holding tank 400 which would also be provided on site. The vacuum is applied to the site vacuum coupler 162; also see FIG. 10, by a hose and any convenient connection fittings. The site vacuum coupler 162 connects to a site vacuum shutoff valve 164 by associated pipe threads (not shown) and the vacuum transfer hose 166. The site vacuum shutoff valve 164 is preferably a standard ball valve which can be manipulated by means of a handle to either allow vacuum to be exerted through the site vacuum shutoff valve 164 or to block flow. The vacuum transfer hose 166 is connected to a pipe nipple threaded into the post port of the drain diverter valve 88 (as previously discussed). A first cross port of the drain diverter valve 88 connects to a check valve 168. The other end of the check valve 168 connects to a multi-purpose hose 158. The check valve 168 blocks liquid flow from the drain diverter valve 88 into the multi-purpose hose 158 if the drain diverter 88 is oriented incorrectly when the tank 52 is pressurized.

The other end of the multi-purpose hose 158 connects to the second cross port of the suction tee 156, reference FIG. 6. The multi-purpose hose 158 is conveniently secured to the second vertical element 24 with at least one (1) tie 41.

Refer now to FIG. 4 which shows a detailed view of a first vacuum pump 172, the second way to draw fluid. The first vacuum pump 172 is preferably a single stage venturi vacuum pump capable of developing a vacuum of approximately twenty five inches of mercury (25 in. Hg) at an input flow of one hundred twenty cubic feet per minute (120 cfm) of air. The first vacuum pump 172 is attached to the first vertical element 22 by a first pump clamp 178 having a clamp fastener 182. The first pump clamp 178 is held to the first vertical element 22 by a clamp securing fastener 184 that passes through the first vertical element 22 and the first pump clamp 178, reference FIG. 6.

The first vacuum pump 172 has a first air inlet 174 which enables the requisite air flow to achieve the desired vacuum. The first vacuum pump 172 is attached through various threaded fittings to an end of a first pump valve 176. The other end of the first pump valve 176 is attached to a first pump elbow 186. The first pump valve 176 is preferably a standard ball valve which can be manipulated by means of a handle to either allow or prevent a vacuum to be exerted through the first pump valve 176 and the first pump elbow 186. The first pump elbow 186 is attached to a first pump inlet 214 of an expansion chamber 212.

FIG. 5 presents a detailed view of a second vacuum pump 192. The second vacuum pump 192 is preferably configured to be any multiple stage venturi vacuum pump capable of developing a vacuum of approximately twenty seven inches of mercury (27 in. Hg) at an input flow of twelve cubic feet per minute (12 cfm) of air. The second vacuum pump 192 is attached to the second vertical element 24 by a second pump clamp 202 having a clamp fastener 182. The second pump clamp 202 is attached to the second vertical element 24 by a clamp securing fastener 184 that is inserted through the second pump clamp 202 and the second vertical element 24, reference FIG. 6.

The second vacuum pump 192 has a second air inlet 194 and an air inlet regulator 196. The air inlet regulator 196 modifies the inlet air pressure within a certain adjustable range so as to allow the application of the requisite air flow to achieve the desired results. The second vacuum pump 192 is attached through various threaded fittings to a second pump valve 204. The second pump valve 204 is also attached to a second pump elbow 206. The second pump valve 204 is preferably a standard ball valve which can be manipulated by means of a handle to either allow or to prevent a vacuum being exerted through the second pump elbow 206. The second pump elbow 206 is attached to a second pump inlet 216 of the expansion chamber 212.

Referring now primarily to FIGS. 2 and 5, a fluid knock out assembly 210 prevents fluid drawn from the subterranean reservoir from entering either the first vacuum pump 172 or the second vacuum pump 192. The fluid knock out assembly 210 includes the expansion chamber 212 and a knock out tube 222. The expansion chamber 212 is a special thermoplastic pipe fitting configured to have four (4) uniformly sized unthreaded female ports and one (1) aperture. Disposed in the side wall of the expansion chamber 212 is a threaded female aperture conforming to one quarter inch National Pipe Thread (¼ in. NPT) into which an expansion gauge 218 is connected. The expansion gauge 218 preferably measures both vacuum and positive pressure in the expansion chamber 212. The first port of the expansion chamber 212 is preferably chemically bonded to the upper end of the knock out tube 222. The second port of the expansion chamber 212 is the first pump inlet 214. A third port of the expansion chamber 212 is a top port 228 through which a vacuum is supplied to the sampling column 100. The top port 228 is located directly opposite the knock out tube 222 so that any fluid entering the expansion chamber 212 will experience a change in velocity due to the increased cross-sectional area of the expansion chamber 212 in comparison to the fittings in the top port 228 and thereby drop into the knock out tube 222. The fourth port of the expansion chamber 212 is the second pump inlet 216.

The knock out tube 222 is preferably configured to be a hollow polycarbonate cylinder. Disposed at a lower end of the knock out tube 222 is a knock out base 223. The knock out base 223 is preferably a PVC coupling having blank female ports. An upper port of the knockout base 223 is affixed to the lower end of the knock out tube 222. The lower port of the knock out base 223 is reduced by appropriate fitting to connect to a first end of a disposal valve 224. A disposal fitting 226 is connected at a second end of the disposal valve 224. The disposal valve 224 is preferably a standard ball valve which can be manipulated by means of a handle to either allow accumulated fluid to pass through the internal chamber to the disposal fitting 226 or to block the chamber to disallow any flow.

Still referring primarily to FIGS. 2 and 5, a first end of a vacuum routing hose 232 is attached to the top port 228 of the expansion chamber 212 by means of another hose clamp 238. A second end of the vacuum routing hose 232 is attached to a first end of a secondary vacuum shut-off valve 234 by means of another hose clamp 238. A second end of the secondary vacuum shut-off valve 234 is connected by threaded fittings to a first cross port of the suction tee 156 as seen in FIG. 6. The secondary vacuum shut-off valve 234 is preferably a standard ball valve which can be manipulated by means of a handle to either allow a vacuum to be exerted through an internal chamber to the suction tee 156 or to block the chamber and disallow any flow.

It may be necessary to incorporate other pipe fittings, such as, but not limited to, elbows, nipples, or reducers, into any portion of the portable analysis device 10 to interconnect the enumerated pieces.

FIG. 11 presents a block diagram of the process flow of the portable analysis device 10. When an external vacuum source is being used, the secondary vacuum shut-off valve 234 is closed. The site vacuum coupler 162 is connected to the site vacuum pump 405 through the holding tank 400. The site vacuum shut-off valve 164 is opened. A vacuum is exerted on the vacuum transfer hose 166, the drain diverter valve 88, the check valve 168, the multi-purpose hose 158, the suction tee 156, and the suction diverter valve 152. The suction diverter valve 152 is adjusted to allow the external vacuum to enter an inlet port of the vacuum cross 122. When the well diverter valve 132 is adjusted fluid is drawn from the subterranean reservoir into the well inlet coupling 134 and through the well diverter valve 132 and through the vacuum cross 122 and into the graduated cylinder 102. In the graduated cylinder 102 the drawn fluid can stratify and its constituents can be measured. At this time the gate valve 112 at the lower end of the sampling column 100 as well as the chemical injection valve 128 and the vent valve 146 must be closed.

When a sufficient quantity of fluid has been drawn into the graduated cylinder 102, the well diverter valve 132 and the suction diverter valve 152 are adjusted to allow flow into the by-pass hose 138 and from there down to the second cross port of the vacuum diverter valve 152; through the post port of the vacuum diverter valve 152; to the post port of the suction tee 156; through the multi-purpose hose 158; through the check valve 168 and to the first cross port of the drain diverter valve 88; then to the post port of the drain diverter valve 88; and into the holding tank 400.

A liquid demulsifier can be injected into the graduated cylinder 102 by connecting the demulsifier to the chemical injection port 129; opening the chemical injection valve 128; opening the vent port 144; and then pressurizing the demulsifier container if required.

When the fluids have stratified the volumes of non-aqueous phase liquids (NAPL) and the water can be measured and recorded.

If a sample of the fluid is required for further analysis a container is positioned at the sampling port 106/sampling valve 108 and the vent valve 146 are opened. Opening the vent valve 146 allows atmospheric pressure into the graduated cylinder 102 which permits fluid to flow out of the sampling valve 108 and into a sampling container.

After the measurements and sampling have taken place the fluid can be emptied from the graduated cylinder 102 into the fluid sump 50 by opening the gate valve 112, the vent valve 146, and the equalization valve 68 on the tank 52. If required another cut of the fluid can be taken by repeating the previous procedure.

If an external vacuum source is not used but a continuous supply of compressed air having a volume of approximately one hundred twenty cubic feet per minute (120 cfm) is available the first vacuum pump 172 can be utilized. The compressed air is connected to the first pump air inlet 174. The first pump valve 176 is opened to allow air flow through the first vacuum pump 172. The air flow through the first vacuum pump 172 creates a vacuum by the venturi effect. The secondary vacuum shut-off valve 234 is opened. With the first pump valve 176 opened a vacuum is exerted on the first pump inlet 214, the expansion chamber 212, the top port 228, the vacuum routing hose 232, the secondary vacuum shut-off valve 234, the suction tee 156, and the suction diverter valve 152. The suction diverter valve 152 is adjusted to exert the vacuum on the vacuum port 142 of the vacuum cross 122 and the upper tee 126. When the well diverter valve 132 is adjusted to draw fluid from the subterranean reservoir, the fluid is drawn into the well inlet coupling 134 through the well diverter valve 132, down through the inlet port 124, through the vacuum cross 122 and finally into the graduated cylinder 102 where the fluid can stratify and be measured. At this time the gate valve 112 at the lower end of the sampling column 100, as well as the chemical injection valve 128 and the vent valve 146 must be closed.

When a sufficient quantity of fluid has been drawn into the graduated cylinder 102 the well diverter valve 132 is adjusted to shut off the flow from the subterranean reservoir. The procedure for measuring and discarding the fluid is the same as described above.

If an external vacuum source or a large volume of air is not available, but a continuous supply of compressed air having a volume of approximately twelve cubic feet per minute (12 cfm) is, the second vacuum pump 192 can be used. In that case the compressed air is connected to the second pump air inlet 194. The air inlet regulator 196 is adjusted to a maximum pressure setting of sixty eight pounds per square inch (68 psi). The air supply valve 198 is opened to allow air flow to the second vacuum pump 192. The air flow into the second vacuum pump 192 creates a vacuum by the venturi effect. The secondary vacuum shut-off valve 234 is opened. The second pump valve 204 is opened and a vacuum is exerted on the second pump inlet 216, the expansion chamber 212, the top port 228, the vacuum routing hose 232, the secondary vacuum shut-off valve 234, the suction tee 156, and the suction diverter valve 152. The suction diverter valve 152 is adjusted to exert the vacuum on the vacuum port 142 of the vacuum cross 122. When the well diverter valve 132 is adjusted fluid from the subterranean reservoir is drawn into the well inlet coupling 134 through the well diverter valve 132, down through the inlet port 124, through the vacuum cross 122 and finally into the graduated cylinder 102 where the fluid can stratify and be measured. At this time the gate valve 112 at the lower end of the sampling column 100, as well as the chemical injection valve 128 and the vent valve 146 must be closed.

When a sufficient quantity of fluid has been drawn into the graduated cylinder 102 the well diverter valve 132 is adjusted to shut off the flow from the subterranean reservoir. The procedure for measuring and discarding the fluid into the fluid sump 50 remains the same as described above.

If fluid is pumped from the subterranean reservoir and transferred to the portable analysis device 10 at a positive pressure the vacuum system is not required. The secondary vacuum shut-off valve 234 remains closed. The site vacuum coupler 162 is connected directly to the holding tank 400. The site vacuum shut-off valve 164 is opened to permit by-pass flow to proceed into the holding tank 400. The fluid flow from the subterranean reservoir must not exceed a pressure of fifteen pounds per square inch (15 psi). The well diverter valve 132 is adjusted to transfer the fluid to the sampling column 100. Fluid is directed into the well inlet coupling 134 and proceed through the well diverter valve 132, down through the inlet port 124, through the vacuum cross 122 and finally into the graduated cylinder 102 where the fluid can stratify and be measured. At this time the gate valve 112 at the lower end of the sampling column 100, as well as the chemical injection valve 128 and the vent valve 146 must be closed.

When a sufficient quantity of fluid has been drawn into the graduated cylinder 102 the well diverter valve 132 is adjusted to allow flow into the by-pass hose 138 and from there to the holding tank 400. The procedure for measuring and discarding the fluid remains the same as described above.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed is:

1. A portable sampling device, comprising:
    a "U" shaped frame comprised of a first vertical element, a second vertical element and a brace across the tops of said first vertical element and said second vertical element, wherein said first vertical element has a first free end and said second vertical element has a second free end;
    a fluid sump having a tank connected to said first free end and to said second free end, said tank including a top inlet valve fitting for allowing fluid into said tank, said fluid sump further including wheels operatively attached to said tank;
    a calibrated sampling column having a graduated cylinder, said sampling column attached to said frame above said fluid sump;
    a cylinder base operatively connected to said inlet valve fitting; and,
    a gate valve disposed between said cylinder base and said sampling column, said gate valve for selectively allowing fluid to drain from said graduated cylinder into said tank.

2. The portable sampling device according to claim 1, further including a U" shaped support arm attached to said first vertical element and to said second vertical element, wherein said support arm forms a handle.

3. The portable sampling device according to claim 1, wherein said wheels are attached by an axle mount fixed to said tank and by an axle coupled to said axle mount.

4. The portable sampling device according to claim 1, further including a sight tube attached to said tank.

5. The portable sampling device according to claim 1, further including a purge fitting for passing material into said tank; a pipe cross operatively connected to said purge fitting, and an air inlet valve attached to said pipe cross, wherein said air inlet valve selectively enables air to pass through said pipe cross into said tank.

6. The portable sampling device according to claim 5, further including a purge gauge operatively connected to said pipe cross, said purge gauge for displaying pressure in said tank.

7. The portable sampling device according to claim 6, further including an equalization valve operatively connecting said pipe cross to an equalization tube, said equalization valve for selectively equalizing pressure in said tank with pressure in said equalization tube.

8. The portable sampling device according to claim 1, further including a drain fitting operatively connected to the bottom of said tank, a drain hose assembly operatively connected to said drain fitting, and a 3-way drain diverter valve operatively connected to said drain fitting, wherein said drain diverter valve for selectively allows fluid in said tank to drain.

9. The portable sampling device according to claim 1, further including a sampling valve operatively connected to said cylinder base, said sampling valve for selectively passing fluid in said graduated cylinder to an external container.

10. The portable sampling device according to claim 1, further including a vacuum cross operatively connected to the top of said graduated cylinder and a cylinder gauge attached to said vacuum cross, wherein said cylinder gauge measures pressure in said vacuum cross.

11. The portable sampling device according to claim 10, wherein said vacuum cross includes a vacuum port for receiving a vacuum for said vacuum cross and an inlet port for receiving drawn fluid.

12. The portable sampling device according to claim 11, wherein said vacuum port is operatively connected to a vacuum shut off valve, and wherein said vacuum shut off valve selectively applies a vacuum to said vacuum port from an external vacuum pump.

13. The portable sampling device according to claim 11, wherein said vacuum port is operatively connected to a pump valve via an expansion chamber, and wherein said pump valve selectively applies a vacuum to said vacuum port from a venturi pump.

14. The portable sampling device according to claim 10, wherein said vacuum cross includes a vent port operatively connected to a vent valve for selectively venting pressure in said vacuum cross.

15. The portable sampling device according to claim 11, wherein said inlet port is operatively connected to said vacuum cross, said inlet port for selectively receiving an input chemical selectively passed by a chemical injection valve.

16. The portable sampling device according to claim 15, wherein said input chemical is a demulsifier.

17. The portable sampling device according to claim 15, wherein said inlet port receives a fluid drawn by vacuum from a reservoir.

18. A sampling device adapted to separate constituents from a fluid by phase stratification, comprising:
    a sampling column configured to receive said fluid from a subterranean reservoir from said subterranean reservoir and temporarily contain said fluid to allow said fluid to be stratified and sampled for further analysis, wherein said sampling column is provided with a sampling valve to selectively allow flow of said fluid into an ancillary container for further analysis;
    a fluid sump in fluid communication with said sampling column configured to selectively receive said fluid from said sampling column to clear said sampling column for repeated infiltration of said fluid therein, wherein said fluid sump is provided with a drain to selectively discharge said fluid from said fluid sump into an ancillary holding tank to clear said fluid sump for repeated infiltration of said fluid therein;
    a vacuum source, comprising:
        a first vacuum pump in fluid communication with said sampling column and said fluid sump;
        a second vacuum pump in fluid communication with said sampling column and said fluid sump; and,
        a vacuum coupler in fluid communication with said sampling column and said fluid sump configured to enable connection to an ancillary vacuum source to provide a motive power to draw said fluid from said subterranean reservoir;
    a fluid knock-out assembly in fluid communication with said sampling column and said fluid sump, comprising:
        an expansion chamber; and, a knock-out tube in fluid communication with said expansion chamber;
wherein each vacuum pump is configured to generate a vacuum through said expansion chamber; and,
wherein said fluid knock-out assembly is configured to prevent fluid from said subterranean reservoir from entering each vacuum pump;
a chemical injection port configured to receive an demulsifier solution and introduce said solution into said sampling column, said chemical injection port provided with a chemical injection valve to selectively allow flow of said solution into said sampling column;
a plurality of valves, hoses, and fittings configured to enable selective routing of said fluid throughout said sampling device; and,
a transport cart, comprising:
  a handled frame having a top, bottom, front, and rear, comprising:
  a first vertical member having at least one first handle aperture;
  a second vertical member having at least one second handle aperture;
  an upper end, said upper end forms a first brace;
  wherein said first vertical member, said second vertical member, and said upper end form a U-shaped arrangement;
  a second brace located between, and in a common geometric plane as, said first vertical member and said second vertical member;
  a U-bolt disposed on said second brace and configured to receive and support said fluid knock-out assembly;
  a third brace affixed to a common face of said first vertical member and said second vertical member between said first brace and said second brace, said third brace having a C-shape that extends out of said geometric plane toward said rear;
  at least two sleeves, comprising:
    a first sleeve affixed to a side of said fluid sump, said first sleeve is provided with at least one third handle aperture; and,
    a second sleeve affixed to a side of said fluid sump, said second sleeve is provided with at least one fourth handle aperture;
  wherein said first sleeve and said second sleeve are configured to receive and secure distal ends of said first vertical member and said second vertical member, respectively;
  a wheeled assembly affixed to a surface of said fluid sump.

19. The device recited in claim 18, wherein said first and second vacuum pumps are each a Venturi pump.

20. The device recited in claim 18, wherein said wheeled assembly includes:
  an axle mount;
  an axle rotatingly affixed to said axle mount;
  at least two wheels rotatingly affixed to distal ends of said axle; and,
  a stand disposed on a bottom surface of said fluid sump;
  wherein said wheeled assembly is configured to form a three-point support in conjunction with each wheel when rested upon said stand so that said sampling device is supported in an up-right position.

* * * * *